United States Patent
Lavery et al.

(10) Patent No.: US 6,485,447 B1
(45) Date of Patent: Nov. 26, 2002

(54) FOOT SUPPORT DEVICE WITH ADJUSTABLE FOREFOOT ROCKER ANGLE

(75) Inventors: Lawrence A. Lavery, San Antonio, TX (US); Dan R. Lanctot, San Antonio, TX (US); Ruben G. Zamorano, San Antonio, TX (US)

(73) Assignee: Salix Medical, Inc., San Antonio, TX (US)

( * ) Notice: Subject to any disclaimer, the term of this patent is extended or adjusted under 35 U.S.C. 154(b) by 0 days.

(21) Appl. No.: 09/578,304

(22) Filed: May 25, 2000

(51) Int. Cl.[7] .................................................. A61F 5/00
(52) U.S. Cl. ......................................... 602/23; 602/27
(58) Field of Search ................................ 602/5, 11, 13, 602/14, 23, 27, 30, 60–62, 65; 128/882, DIG. 20; 36/3 A, 3 R, 29, 35 B

(56) References Cited

U.S. PATENT DOCUMENTS

| | | | | |
|---|---|---|---|---|
| 4,962,760 A | * | 10/1990 | Jones | 602/27 |
| 4,977,891 A | * | 12/1990 | Grim | 602/27 |
| 4,999,932 A | * | 3/1991 | Grim | 36/88 |
| 5,078,128 A | | 1/1992 | Grim et al. | 128/83.5 |
| 5,092,321 A | * | 3/1992 | Spademan | 602/27 |
| 5,352,189 A | * | 10/1994 | Schumann | 602/27 X |
| 5,464,385 A | * | 11/1995 | Grim | 602/27 |
| 5,496,263 A | * | 3/1996 | Fuller, II | 602/27 |
| 5,706,589 A | * | 1/1998 | Marc | 36/27 |
| 5,813,140 A | * | 9/1998 | Obeid | 36/3 R |
| 5,976,099 A | | 11/1999 | Kellogg | 602/23 |
| 6,134,812 A | * | 10/2000 | Voss | 36/29 |
| 6,142,968 A | * | 11/2000 | Pigg | 602/75 |
| 6,152,893 A | * | 11/2000 | Pigg | 602/75 |
| 6,177,171 B1 | * | 1/2001 | Constantinides | 428/101 |

FOREIGN PATENT DOCUMENTS

WO     WO97/39709     10/1997

* cited by examiner

Primary Examiner—Denise M. Pothier
(74) Attorney, Agent, or Firm—Jenkens & Gilchrist A Professional Corporation

(57) ABSTRACT

A foot support device for use on the foot of a human being includes a foot cradle. The foot cradle has a rear portion and a hinged forefoot support portion. The hinged forefoot support portion may be set at a rocker angle which is the most beneficial for the patient. The foot support device is attached to the foot and lower leg of the wearer with binders.

16 Claims, 3 Drawing Sheets

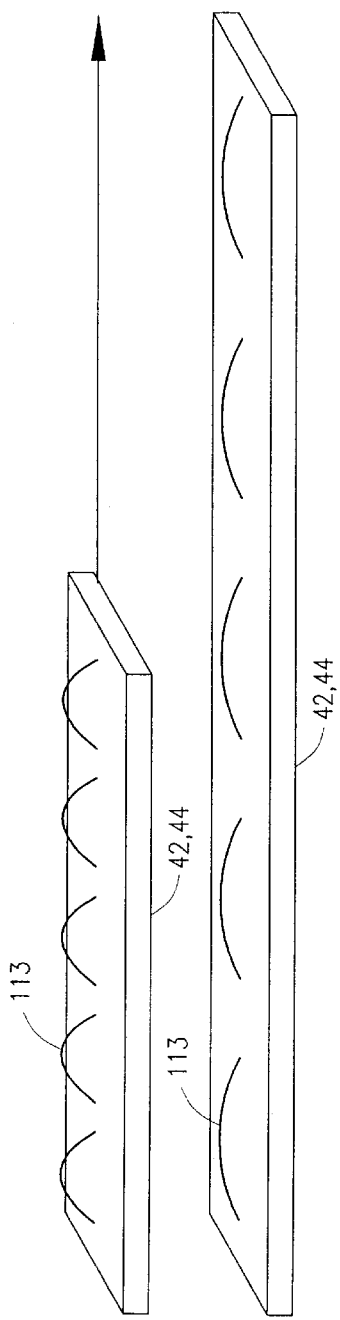
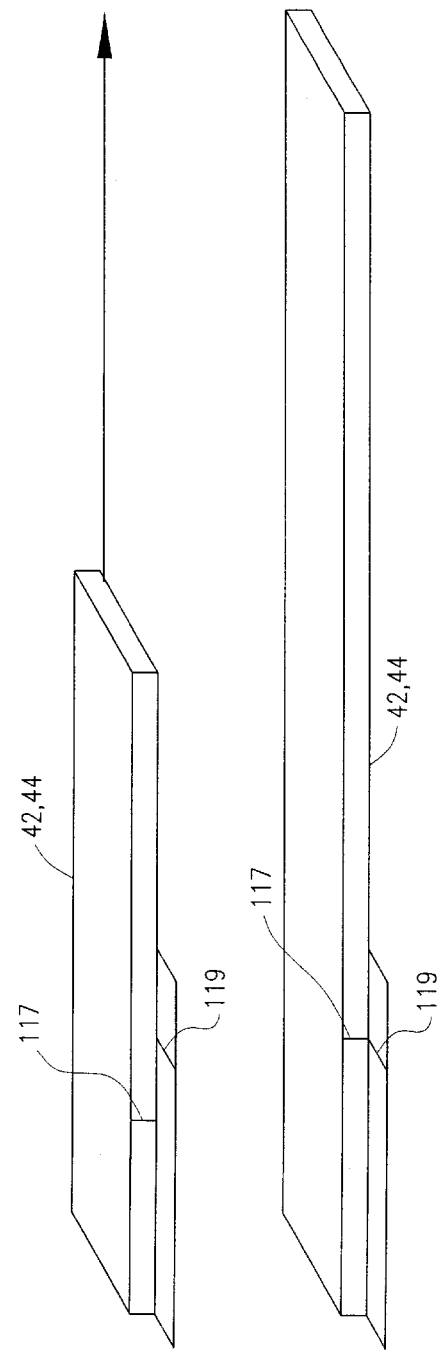

FOOT SUPPORT DEVICE WITH ADJUSTABLE FOREFOOT ROCKER ANGLE

FIELD

The present invention pertains to a foot support device; more particularly, the present invention pertains to a foot support device which enables a person with orthopedic trauma or a podiatric injury or malady to ambulate such that the weight of the wearer's body is spread over the bottom of the wearer's foot.

BACKGROUND

It has become common in the treatment of orthopedic foot and ankle or podiatric injuries for medical care professionals to place the foot of a patient in a foot support device, often called a removable cast walker. Such removable cast walkers are strapped to the foot and the lower leg of the patient. Cast walkers often include a rigid base. The shape of the rigid base determines the gait of the patient. For example, a patient who wears a walker with a rigid flat base is forced into an apropulsive shuffle type gait. A walker with more of a rocker angle or curvature on its base or outer sole enables easier ambulation during gait.

For patients who have a tendency to develop ulcers on their feet, typically patients with diabetes, there is a need to spread the weight of the patient's body over the bottom of the patient's foot to reduce the force concentration on that portion of the foot where the ulcer has formed. Initially, even distribution of the weight of the patient's body weight over the bottom of the foot requires a walker with a flat bottom; but as the ulcer heals, the patient is able to tolerate more rocker angle in the base to allow a more normal gait characterized by rolling/rocking off the front of the foot). That is, as the ulcer heals, the patient becomes more able to bear weight and push off the front portion of the foot when walking. Unfortunately, the use of prior art removable cast walkers with a rigid flat base constrains a patient with foot ulcers to a single base profile during the entire healing process whether the patient is able to tolerate a more normal gait or requires a shuffle type gait.

There is therefore a need in the art to provide a removable cast walker for a patient with foot problems particularly ulcers, which includes a base whose rocker angle can be adjusted so that a patient's gait may be gradually returned to a more normal gait during the healing process.

SUMMARY

The foot support device of the present invention allows the adjustment of the rocker angle during the healing process.

The foot support device of the present invention includes a base whose contour may be gradually adjusted from a flat contour to an angled contour during the healing process. Specifically, the disclosed foot support device is constructed to be worn over the bottom of a patient's foot and attached to the lower leg. When properly worn, the foot support device of the present invention enables the wearer to initially distribute the body weight over the bottom of the foot and along the lower leg by using a flat base or rocker profile; and then, while an orthopedic or podiatric injury or malady is healing, to gradually return to a more normal gait by appropriately adjusting the rocker angle.

The lower portion of the disclosed foot support device includes a foot support cradle which has an outer surface, a central portion, and a forefoot portion. The angle of the forefoot portion with respect to the central portion (the rocker angle) is adjustable to enable the patient to move from an initial shuffle type gait in the beginning of the healing process to a more normal gait toward the end of the healing process. The foot of the wearer rests against an insole surface on the foot cradle.

Extending upwardly from either side of the central portion of the foot cradle are a pair of columns or elongated side supports. The columns or elongated side supports extend upwardly along the sides of the wearer's leg. Attached to the elongated side supports and to the foot cradle are binders which secure the foot cradle portion of the and the columns or elongated side supports to the lower leg of the wearer.

The forefoot portion of the foot cradle is hingedly attached to the central portion of the foot cradle. This hinged attachment enables the gradual changing of the contour of the outer portion of the foot cradle to provide a rocker angle under the patient's forefoot which meets both the gait and the medical needs of an individual wearer.

The foot support device may also include a high traction surface on its bottom or lower outer surface.

The binders used to attach the foot support device to the wearer may be elastic straps. The binders may also include force indicators which indicate when an appropriate tightness of the binders has been achieved on the patient's leg.

In an alternate embodiment, the foot support device of the present invention includes an air circulation system with provisions for either an on-board or an external air pump. The on-board air pump includes a resilient bladder which gathers air with each step. The air gathered in the resilient bladder is then used to provide an airflow adjacent to the skin of the wearer each time the wearer takes a step and compresses the resilient bladder.

While a thick padded liner or softgood sock is typically worn over the patient's foot and lower leg while wearing the foot support device of the present invention, the foot support device may include a shear modulation attachment system to minimize any ulceration which may be caused by rubbing against the wearer's skin at the bottom of the foot, on the side of the foot, or below the knee at any point.

BRIEF DESCRIPTION OF THE DRAWING FIGURES

A better understanding of the foot support device with adjustable forefoot rocker angle of the present invention may be had by reference to the drawings wherein:

FIG. 4 is a perspective view of a first system for determining the tightness of the binders; and FIG. 5 is a perspective view of a second system for determining the tightness of the binders.

DESCRIPTION OF THE EMBODIMENTS

Figure 1:
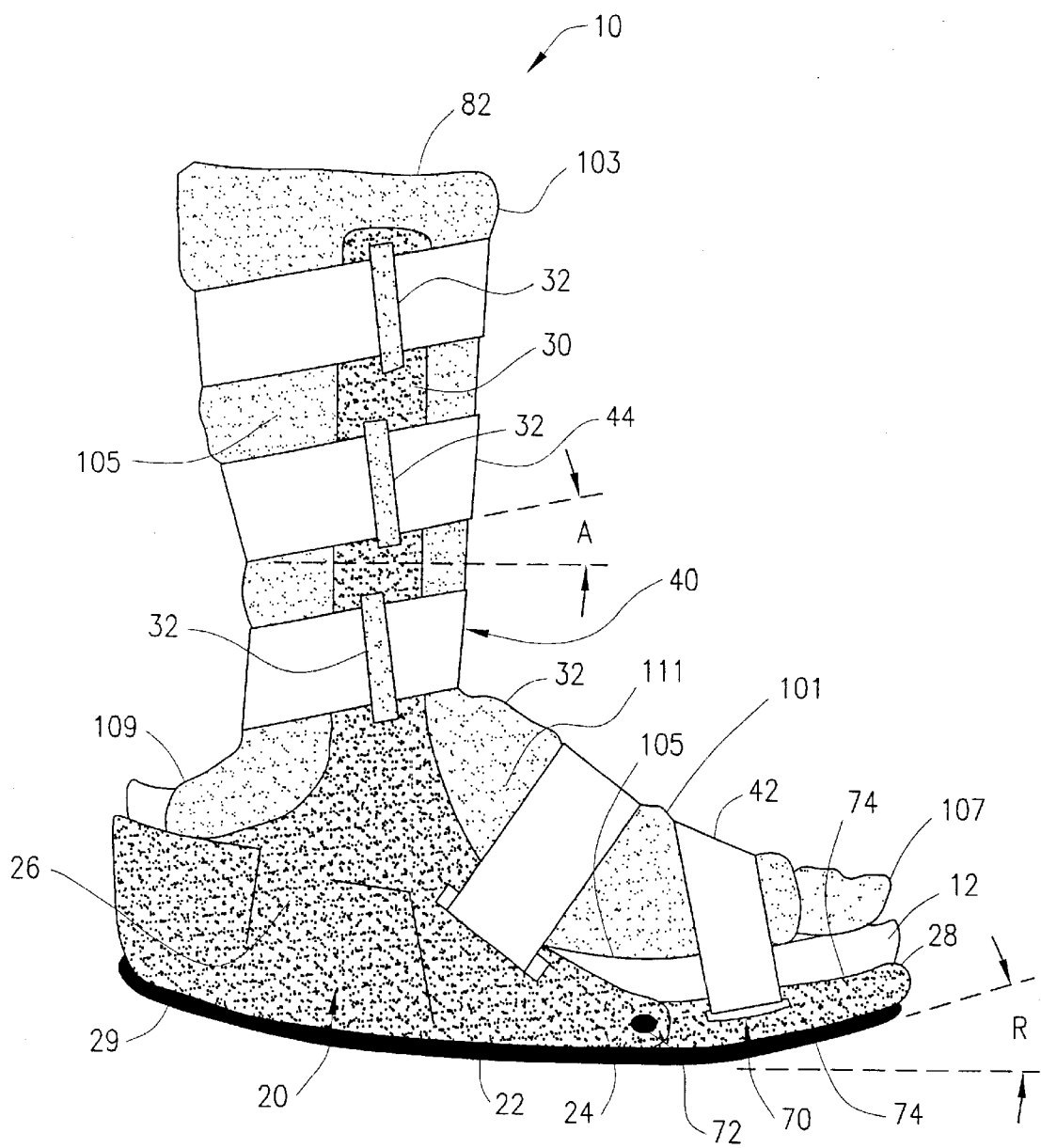
FIG. 1 is a side elevational view of the lower leg and foot of a patient with the foot support device of the present invention attached thereto.

As shown in FIG. 1, the foot support device with adjustable forefoot rocker angle 10 of the present invention is constructed and arranged to be worn under the foot 101 while affixed to the lower leg or calf 103 of a patient. The purpose of the disclosed foot support device 10 is to enable a person to ambulate on a foot where off-loading of the wearer's body weight is required due to orthopedic or podiatric problems such as an open foot ulcer commonly associated with diabetes. Other orthopedic or podiatric problems requiring the use of the foot support device 10 may include blisters, ulcers, other skin or soft tissue-related maladies, and broken bones. The foot support device of the present invention 10 is designed to be temporarily removable from the foot 101 and the lower leg 103 of the patient for the purpose of rest, bathing, or sleep.

The foot support device of the present invention 10 is built about a foot cradle assembly 20. The foot cradle assembly 20 includes a pair of vertically extending columns or supports 30. The columns 30 pass along the side 105 of the lower leg or calf 103 and may extend as high as the wearer's knee (not shown). Also included in the foot support device of the present invention 10 is a binder assembly 40 for attaching the foot cradle assembly 20 to the foot 101 and to the leg 103 of the wearer.

Figure 2:
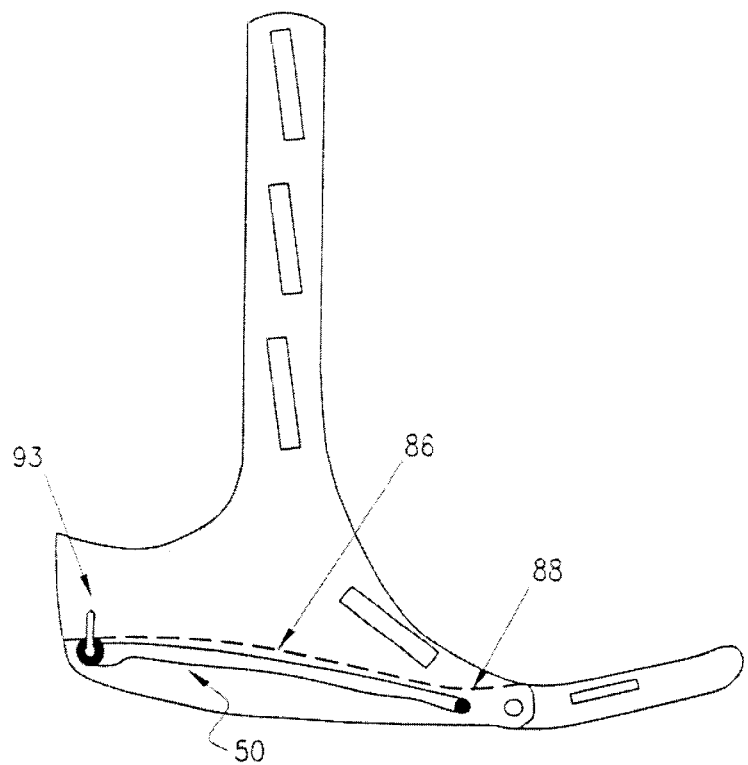
FIG. 2 is a side elevational view of the foot support device showing the optional system for managing air flow.

In the alternate embodiment shown in FIG. 2, the foot support device of the present invention 10 includes an air circulation system 50, and a pressure and shear force reducing system. Key to the foot support device of the present invention 10 and as shown in FIG. 1 is the adjustable forefoot assembly 70 which provides for an adjustable rocker angle R, as will be described below.

The foot cradle assembly 20 is a shoe or sandal-like portion that has vertically extending supports 30 extending upwardly along the sides 105 of the lower leg or calf 103 of the wearer. As may be seen from FIG. 1, the foot cradle assembly, 20 has an outer surface 22 which contacts the floor or ground over which the wearer ambulates, an outer edge 24, a central portion 26 having two sides, and an insole surface 28. The forefoot support assembly 70 is hingedly attached 72 to the foot cradle assembly 20.

The central portion 26 of the foot cradle assembly 20 and the forefoot support assembly 70 are fixed or attached to the foot 101 of the wearer using a first set of binders 42.

The vertically extending supports 30 are attached to the lower leg 103 of the wearer using a second set of binders 44. In one embodiment, the outer surface 22 of the foot cradle assembly has a high traction surface 29 which prevents slippage. As may be seen in FIG. 1, the outer surface 22 of the foot cradle assembly 20 is contiguous with the outer surface 74 of the forefoot support assembly 70 to enable a rocking motion of the foot 101 during ambulation and an even distribution of forces.

The shape of the contiguous surface is adjusted at the hinged portion 72 to provide various rocker angles R which give the greatest clinical benefit to the wearer. For example, in the initial stages of the healing process angle R is substantially zero. As the healing process progresses angle R is increased by a medical professional to a level that can be both tolerated by the patient and not impair the healing process. Another clinical application of the variable rocker angle will be to adjust to different gait patterns. For instance, geriatric patients often have an apropulsive gait and will require a walker with zero angle, while a younger patient with a propulsive gait pattern will use a rocker angle of 20°. As shown in FIG. 1, a cushion or pad 12 may be placed between the bottom 105 of the wearer's foot 101 and the insole surface 28 of the foot cradle assembly 20 and the insole surface 74 of the forefoot support assembly 70 extending from the toe 107 to the heel 109 and under the instep 111.

The binder system 40 for the foot support device of the present invention 10 uses two sets of binding straps 42, 44 which attach the foot cradle assembly 20 and the forefoot support assembly 70 to the foot 101 and to the lower leg 103. In the preferred embodiment, flexible elastic straps are used which are actually tightened around the lower leg 103 and the foot 101. Other embodiments may use flexible non-elastic straps made from canvas, leather, or a polymer non-elastic straps with hook-and-loop or Velcro® fasteners, or alternatively, rigid binders made from either plastic or metal. If flexible elastic straps are used, such flexible straps may include force indicators which will indicate when an appropriate tightness of the flexible straps has been achieved. For example, and as shown in FIG. 4 the flexible straps 42, 44 may include a colored thread 113 which changes its appearance once a desired level of tightness has been achieved. Alternatively, and as shown in FIG. 5 the flexible straps 42, 44 may include a first mark 117 and second mark 119 to which one strap is stretched to achieve the appropriate level of tightness. Such force indicating systems are particularly helpful for those patients who have experienced reduced sensitivity in their lower limbs.

In the illustrated embodiment, the binding straps 42, 44 are placed at an acute angle A to the lower leg 103 to enhance the transfer of vertical load forces from the body weight of the wearer to the lower leg 103. As may be seen in FIG. 1, an air-permeable softgood liner or sock 82 is preferably placed over the lower leg 103 and foot 101 of the wearer.

Figure 3:
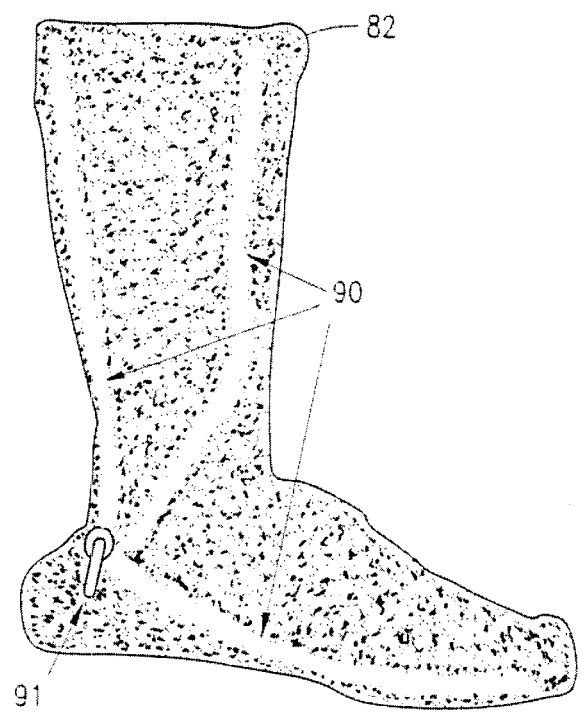
FIG. 3 is a side elevational schematic view of the sock which covers the patient's lower leg including the optional air flow system.

In the alternate embodiment shown in FIG. 3, the air permeable liner 82 may contain a plurality of perforated tubing 90 emanating from a sock intake tube 91. Air flow through the perforated tubes 90 in the air permeable sock 82 is actuated by the ambulation of the wearer. As shown in FIG. 2 air circulation emanates from a resilient air bladder 86 positioned on the insole surface 28 of the foot assembly 20. The resilient air bladder 86 gathers air each time it expands from a compressed state and, when compressed, the resilient air bladder 86 pushes air through the perforated tubing in liner 82. The small holes or perforations in the air 90 contained in the sock 82 permit circulation of air along the interface between the foot support device 10 and the wearer's skin.

The resilient air bladder 86 may include a one-way air intake valve 88. The air output port 93 from the bladder 86 is connected by air intake port 91 on the sock 82 to the plurality of perforated tubes 90. The perforated tubing 90 carries air close to the skin surface of the wearer. This circulation of air may be used to cool the surface of the skin and to prevent the accumulation of any perspiration or fluids on the skin surface of the wearer. If the wearer is at rest, a small air pump, such as used with a fish tank, may be connected to the port 91 on the sock 82 to maintain the flow of air through the perforated tubing 90.

As shown in FIG. 1, the cushion or pad 12 placed on the insole surface 28 of the foot cradle assembly 20 may include a shear modulation system to provide even greater comfort to the wearer. Such shear modulation system is described in pending application Ser. No. 09/109,669 filed Jul. 2, 1998 which is assigned to the same owner as the instant application and incorporated herein by reference. The rubbing friction created at the interface between the bottom 105 of the foot 101 and the liner or sock 82 is one that could contribute to potential ulceration, blistering, or sores on the wearer's skin. In one embodiment, the shear modulation system may actually extend around the exterior axis of the foot 101 from the tip of the toes 107 to the heel 109 and extend along the outer edges 24 of the foot cradle assembly 20 all the way under the instep 111 of the foot 103. In yet another embodiment, the shear modulation system could extend upwardly in a substantially vertical plane along a portion of the ankle or calf 103 either laterally or medially, or just in one plane so that the interior portion of the calf would be prevented from engaging or rubbing against the binding system 20 or the foot cradle assembly 20.

The forefoot support assembly 70 of the foot support device of the present invention 10, as previously indicated, is designed to provide an adjustable rocker angle R. Rocker angle R is set to accommodate the needs of each particular patient. In prior art foot support devices, there is a rigid toe cage which extends from the front of the foot support device. In the instant invention, the forefoot support assembly 70 removes pressure from the toes 107 and additionally may be used to regulate, that is increase or decrease, the "toe-off" gait propulsion experienced during ambulation.

OPERATION

The foot support device with adjustable forefoot rocker angle of the present invention 10 is initially fit to the wearer by an orthopedist, a podiatrist, or a general practice medical practitioner treating an injury or a disease of the foot of a human being. The patient's foot 101 is first placed within the foot cradle assembly 20 and the rocker angle R is established by rigidly fixing the hinge connection 72 between the forefoot support assembly 70 and the foot cradle assembly 20. As previously indicated, the rocker angle R will be relatively small or flat in the early stages of the healing process. At this setting, walking is achieved using a shuffle gait. The sock 82 is fabricated from a material which will wick the perspiration away from the skin surface, then absorb the perspiration. In the preferred embodiment, the air circulation system will aid in the removal of moisture from the skin surface.

The rocker angle R may be fixed by utilization of a lock nut on a threaded fastener or a variety of other mechanical attachment means well known to those of ordinary skill in the art. Such mechanical attachment means will cause the forefoot support assembly 70 to remain in a constant angular relationship with the foot cradle assembly 20.

Once the rocker angle R has been set or re-set, the foot support device 10 is then affixed to the foot 101 and lower leg 103 of the patient. This affixation is accomplished by the use of a binder system 40. In the embodiment where force indicators, such as shown in FIG. 4 and FIG. 5 are used, flexible binding straps 42, 44 may be set at a predetermined tension.

As shown in FIG. 1, the first set of binding straps 44 which surround the lower leg 103 of the patient may be connected to the vertically extending columnar support members 30 by a series of loops 32. These loops 32 not only provide a pathway for the second set of binding straps 44, but also guide the second set of binding straps 44 to an acute angle A which allows the transfer of more vertical load from the patient's body weight to the patient's lower leg 103 rather than to the bottom 105 of the patient's foot 101. Because patients with foot maladies often lose feeling in their lower extremities, the binding straps 42, 44 can easily be under or over tightened. To prevent this from occurring, two systems for establishing the needed amount of adjusting or tightness are disclosed. The first system disclosed in FIG. 4 includes a colored thread 113. When the binding straps 42, 44 are properly tightened, the colored thread 113 small loops which appear as a dashed line. The second system, as shown in FIG. 5 includes a first mark 117 and a second mark 119. When the two marks 117, 119 are aligned the binder has been property adjusted or tightened.

In an alternative embodiment, an air permeable sock or liner 82 is placed over the foot 101 and the lower leg 103 of the patient before the foot support device of the present invention 10 is attached to the patient's foot 101. The air permeable sock 82 prevents chafing by absorbing moisture. If an air circulation system is used, the air output port 93 on the walker is connected to the air intake port 91 on the sock 82. Air will then flow from the resilient air bladder 86 into the air tubing 90 and then exit through the perforations in the tubing 90. This air flow cools the lower leg and reduces perspiration.

In an alternate embodiment, an inflatable bladder can be inserted beneath the foot. This bladder can be divided into separate compartments, each of which can individually be filled with fluid or gas. The fluid or gas pressure in each can be adjusted independently to offload different parts of the foot or to maximize comfort.

It will be understood by those of ordinary skill in the art that the foot support device with adjustable forefoot rocker angle of the present invention 10 has been disclosed by reference to its preferred and alternate embodiments. Still other embodiments of the foot support device of the present invention may be enabled by an understanding of the preferred and alternate embodiments described above. Such other embodiments shall be included within the scope and meaning of the appended claims.

What is claimed is:

1. A foot support device worn over the bottom of the foot and attached to the lower leg which enables the wearer to ambulate on a foot that requires off-loading due to medical problems comprising:

a foot cradle including an outer surface, a central portion, a forefoot portion, and an insole surface;

a pair of columnar supports attached to either side of said central portion of said foot cradle, each of said pair of columnar supports extending upwardly along the lower leg of the wearer;

a first set of binders for securing said foot cradle to the foot of the wearer;

a second set of binders for securing said pair of columnar supports to the lower leg of the wearer;

said forefoot portion of said foot cradle being hingedly attached to said central portion of said foot cradle;

means for rigidly fixing said hinged attachment of said forefoot portion of said foot cradle to said central portion of said foot cradle;

whereby the contour of the outer portion of the foot cradle may be fixedly adjusted to a predetermined rocker angle by moving said forefoot portion at said hinged attachment and then rigidly fixing the angle of said forefoot portion of said foot cradle with respect to said central portion of said foot cradle to provide a rocker angle which meets the gait and medical needs of the wearer.

2. The foot support device as defined in claim 1 further including a high traction surface on said outer surface or bottom of said foot cradle.

3. The foot support device as defined in claim 1 wherein the contour of said outer surface of said foot cradle is changed by movement of said forefoot portion with respect to said central portion to provide a substantially even distribution of forces during ambulation.

4. The foot support device as defined in claim 1 wherein said first set of binders includes elastic or adjustable straps.

5. The foot support device as defined in claim 4 wherein said first set of binders includes force indicators.

6. The foot support device as defined in claim 1 wherein said second set of binders includes elastic straps.

7. The foot support device as defined in claim 5 wherein said second set of binders includes force indicators.

8. The foot support device as defined in claim 1 wherein said second set of binders is placed at a non-perpendicular angle with respect to the lower leg of the wearer.

9. The foot support device as defined in claim 1 further including an air permeable softgood liner or sock constructed and arranged to cover the skin of the wearer.

10. The foot support device as defined in claim 1 wherein said foot cradle includes means for gathering air and causing said gathered air to flow adjacent to the skin of the wearer.

11. The foot support device as defined in claim 10 wherein said means for gathering air includes a resilient bladder and a one-way intake valve.

12. The foot support device as defined in claim 10 wherein said means for gathering air and causing said gathered air to flow adjacent to the skin of the wearer includes tubing to direct the flow of said air.

13. The foot support device as defined in claim 1 wherein a shear modulation system is placed on said insole portion.

14. The foot support device as defined in claim 13 wherein said shear modulation system extends from the toe to the heel of the wearer.

15. The foot support device as defined in claim 13 wherein said shear modulation system extends along the outer edges of said foot cradle.

16. The foot support device as defined in claim 1, further including a shear modulation system sized and configured to extend upwardly along the lower leg of the wearer.

* * * * *